United States Patent
Olejnik et al.

(10) Patent No.: US 7,057,031 B2
(45) Date of Patent: Jun. 6, 2006

(54) NUCLEOTIDE COMPOSITIONS COMPRISING PHOTOCLEAVABLE MARKERS AND METHODS OF PREPARATION THEREOF

(75) Inventors: Jerzy Olejnik, Brookline, MA (US); Edyta Krzymanska-Olejnik, Brookline, MA (US); Kenneth J. Rothschild, Newton, MA (US)

(73) Assignee: AmberGen, Inc., Waltham, MA (US)

( * ) Notice: Subject to any disclaimer, the term of this patent is extended or adjusted under 35 U.S.C. 154(b) by 605 days.

(21) Appl. No.: 10/193,781

(22) Filed: Jul. 12, 2002

(65) Prior Publication Data

US 2003/0099972 A1 May 29, 2003

Related U.S. Application Data

(60) Provisional application No. 60/305,490, filed on Jul. 13, 2001.

(51) Int. Cl.
*C07H 21/00* (2006.01)
*C07H 21/02* (2006.01)
*C12Q 1/68* (2006.01)

(52) U.S. Cl. .................. 536/25.3; 536/23.1; 536/26.6; 435/6; 435/91.1

(58) Field of Classification Search .................. 435/6, 435/91.1; 536/23.1, 25.3, 26.6
See application file for complete search history.

(56) References Cited

U.S. PATENT DOCUMENTS 4,711,955 A * 12/1987 Ward et al. ............... 536/25.32
5,558,991 A    9/1996 Trainor et al. .................. 435/6

FOREIGN PATENT DOCUMENTS

WO    WO 99/19341    4/1999
WO    WO 00/53812    9/2000

OTHER PUBLICATIONS

Hausch et al. Tetrahedron Letters, 39, 1998, 6157-6158.*
Drmanac et al., "Accurate sequencing by hybridization for DNA diagnostics and individual genomics," *Nature Biotechnol.*, 16, 54-58 (1998).
I. Hemmila, "Applications of Fluorescence in Imunoassays," Chap 7.4 *Organometallic Fluorochromes*, pp. 139-158, Wiley-Interscience, New York, 1991.
RD Mitra and GM Church, "*In situ* localized amplification and contact replication of many individual DNA molecules," *Nucl. Acids Res.*, 27(4): i-vi (1999).
Olejnik et al., "Photocleavable Affinity Tags for isolation and Detection of Biomolecules," *Methods Enzymol.*, 291:135-54 (1998).
Patchornik et al., "Photo Protecting Groups," *J. Am. Chem, Soc.* 92:6333-35 (1970).
V.N. Rajasekharan Pillai, "Photoremovable Protecting Groups in Organic Synthesis," *Synthesis*, 1:1-26 (1980).
Ronaghi et al., "DNA Sequencing: A Sequencing Method Based on Real Time Pyrophosphate," *Science*, 281:363-365 (1998).

* cited by examiner

*Primary Examiner*—Jezia Riley
(74) *Attorney, Agent, or Firm*—Medlen & Carroll, LLP

(57) ABSTRACT

Labelled nucleotides and polynucleotides useful in the sequencing of nucleic acids are described. Methods of preparing photocleavable marker nucleotides and photocleavable marker-polynucleotide conjugates are described. Such photocleavable markere nucleotides can be incorporated into nucleic acid so as to create photocleavable marker-polynucleotide conjugates.

11 Claims, 13 Drawing Sheets

M = marker

S = sugar (ribose, deoxyribose, dideoxyribose and analogs)

M = marker

S = sugar (ribose, deoxyribose, dideoxyribose and analogs)

M = marker

S = sugar (ribose, deoxyribose, dideoxyribose and analogs)

M = marker

SEQUENCE LISTING

<160> NUMBER OF SEQ ID NOS: 1

<210> SEQ ID NO 1
<211> LENGTH: 30
<212> TYPE: DNA
<213> ORGANISM: Homo sapiens

<400> SEQUENCE: 1
gtatctatat tcatcatagg aaacaccaca                                          30

NUCLEOTIDE COMPOSITIONS COMPRISING PHOTOCLEAVABLE MARKERS AND METHODS OF PREPARATION THEREOF

This application is a provisional of Ser. No. 60/305,490 filed Jul. 13, 2001.

FIELD OF THE INVENTION

The present invention generally relates to nucleotides and polynucleotides useful in the sequencing of nucleic acids. The present invention specifically relates to compositions comprising nucleotides and polynucleotides comprising photocleavable labels and the methods of preparing said compositions.

BACKGROUND OF THE INVENTION

The sequencing of nucleic acids is one the most powerful and valuable tools for scientific research. As evidenced by the Human Genome project, there is an ever increasing demand for nucleic acid sequence information. There are numerous methods available for sequencing of nucleic acids. The first methods were developed almost twenty years ago. For example, the Sanger enzymatic (i.e., dideoxy chain termination) method involves synthesis of a DNA strand from a single-stranded template by a DNA polymerase. The Maxam and Gilbert method involves chemical degradation (i.e. chemical cleavage) of the original DNA. Both methods produce populations of radio-labelled polynucleotides that begin at a fixed point in the DNA to be sequenced and terminate at points which are dependent upon the location of a particular base in the original DNA strand. These polynucleotides are separated by a polyacrylamide gel electrophoresis, and the order of the nucleotides in the original DNA is directly read from an autoradiograph of the gel. However, the time-consuming electrophoresis step associated with these methods is difficult to perform in a highly parallel (i.e. greater than 1000 samples at a time per instrument) fashion.

Although both the Sanger and Maxam-Gilbert methods are currently used, there have been many changes and improvements. The enzymatic chain termination method is probably the most popular and widely used technique for sequence determination, especially since the automation of the procedure has been accomplished through use of fluorescent, rather than radioactive labelling, and the utilization of amplification technology. The incorporation of amplification technology (e.g., the polymerase chain reaction [PCR]) enables the sequencing reaction to be cycled. Other advances include sequencing by chemiluminescence, multiplexing, and solid phase sequencing.

Other nucleic acid sequencing methods, such as sequencing by hybridization and pyrosequencing, have been developed that eliminate the electrophoresis step associated with the Sanger and Maxam and Gilbert methods, thereby allowing more samples to be sequenced in parallel. However, such methods often involve either lengthy cloning and amplification steps, or a time-consuming chemical cleavage step wherein a fluorescently-labeled polynucleotide is removed by enzymatic digestion.

Therefore, what is need is are compositions and methods that reduce the complexity of and time-consuming nature of parallel nucleic acid sequencing.

SUMMARY OF THE INVENTION

The present invention generally relates to nucleotides and polynucleotides useful in the sequencing of nucleic acids. The present invention specifically relates to compositions comprising nucleotides and polynucleotides comprising photocleavable labels and the methods of preparing said compositions.

The present invention contemplates compositions comprising photocleavable marker-polynucleotide conjugate compounds having the general formula (I):

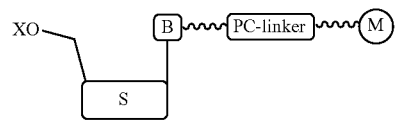

wherein X is selected from the group consisting of a phosphate group and a hydrogen atom, M is a photocleavable marker, B is a nucleobase, PC-linker is a photocleavable linker, and S is a sugar moiety.

It is not intended that the compounds of general formula (I) be limited to a specific phosphate group. In one embodiment, said phosphate group is a monophosphate group, more preferably a polyphosphate such as a diphosphate group, and even more preferably a triphosphate group. In another embodiment, said phosphate group is a pyrophosphate.

It is not intended that the nucleobase of the compounds of general formula (I) be limited to a specific nucleobase. In one embodiment, said nucleobase is selected from the group consisting of adenine, cytosine, guanine, thymine, uracil, and analogs thereof such as, for example, acyclic nucleobases.

It is not intended that the sugar moiety of the compounds of general formula (I) be limited to a specific sugar moiety. In one embodiment, said sugar moiety selected from the group consisting of ribose, deoxyribose, dideoxyribose, and analogs thereof.

It is not intended that the photocleavable linker of the compounds of general formula (I) be limited to a specific photocleavable linker. In one embodiment, said photocleavable linker is a photocleavable linker comprising a protective group selected from the group consisting of 9-fluorenylmethoxycarbonyl (Fmoc), 2-(4-biphenyl)propyl(2) oxycarbonyl (Bpoc), and derivatives thereof.

It is not intended that the compounds of general formula (I) be limited to any specific photocleavable marker. In one embodiment, said photocleavable marker is BODIPY-FL. In another embodiment, said photocleavable marker is Cy5.

It is not intended that the photocleavable marker of the compounds of general formula (I) be detected by any specific method. In one embodiment, said photocleavable marker is a binding member and is detected via a second binding member. In another embodiment, said photocleavable marker is a molecule that can be detected by mass spectrometry. In another embodiment, said photocleavable marker is a fluorescent moiety and can be detected by fluorescence spectroscopy. In a further embodiment, said photocleavable marker is a chelator capable of forming luminescent complexes.

The present invention also contemplates compositions comprising photocleavable marker-polynucleotide conjugate compounds having the general formula (II):

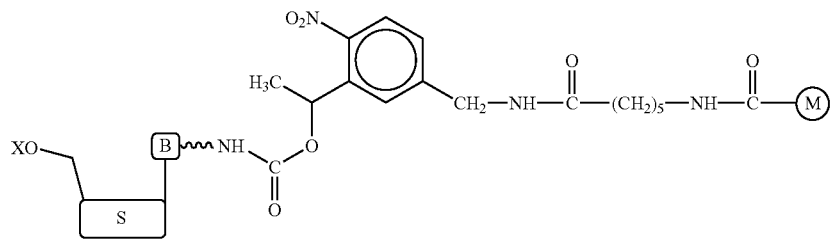

wherein X is selected from the group consisting of a phosphate group and a hydrogen atom, M is a photocleavable marker, B is a nucleobase, and S is a sugar moiety.

It is not intended that the compounds of general formula (II) be limited to a specific phosphate group. In one embodiment, said phosphate group is a monophosphate group, more preferably a polyphosphate such as a diphosphate group, and even more preferably a triphosphate group. In another embodiment, said phosphate group is a pyrophosphate.

It is not intended that the nucleobase of the compounds of general formula (II) be limited to a specific nucleobase. In one embodiment, said nucleobase is selected from the group consisting of adenine, cytosine, guanine, thymine, uracil, and analogs thereof such as, for example, acyclic nucleobases.

It is not intended that the sugar moiety of the compounds of general formula (II) be limited to a specific sugar moiety. In one embodiment, said sugar moiety selected from the group consisting of ribose, deoxyribose, dideoxyribose, and analogs thereof.

It is not intended that the photocleavable linker of the compounds of general formula (II) be limited to a specific photocleavable linker. In one embodiment, said photocleavable linker is a photocleavable linker comprising a protective group selected from the group consisting of 9-fluorenylmethoxycarbonyl (Fmoc), 2-(4-biphenyl)propyl(2)oxycarbonyl (Bpoc), and derivatives thereof.

It is not intended that the compounds of general formula (II) be limited to any specific photocleavable marker. In one embodiment, said photocleavable-marker is BODIPY-FL. In another embodiment, said photocleavable marker is Cy5.

It is not intended that the photocleavable marker of the compounds of general formula (II) be detected by any specific method. In one embodiment, said photocleavable marker is a binding member and is detected via a second binding member. In another embodiment, said photocleavable marker is a molecule that can be detected by mass spectrometry. In another embodiment, said photocleavable marker is a fluorescent moiety and can be detected by fluorescence spectroscopy. In a further embodiment, said photocleavable marker is a chelator capable of forming luminescent complexes.

The present invention also relates to methods of preparing photocleavable marker nucleotides. For example, in one embodiment, the present invention contemplates a method of preparing a marker-photocleavable linker-nucleotide conjugate ("photocleavable marker nucleotide") comprising: a) providing i) a photocleavable linker comprising a protective group, ii) a nucleotide (or analog thereof), and iii) an activated marker molecule; b) operably linking said photocleavable linker to said nucleotide (or analog thereof) to produce a photocleavable linker-nucleotide conjugate; c) removing said protective group from said photocleavable linker-nucleotide conjugate under conditions such that an activated photocleavable linker-nucleotide conjugate is created, wherein said activated photocleavable linker-nucleotide conjugate has an exposed reactive site on the linker portion of the conjugate; and d) contacting said activated marker molecule with said activated photocleavable linker-nucleotide conjugate under conditions such that a marker-photocleavable linker-nucleotide conjugate is produced. In a preferred embodiment, the method of the present invention produces a photocleavable marker nucleotide comprising a nucleotide 5'-triphosphate.

Importantly, in a preferred embodiment, the conditions for step c) are chosen such that the integrity of said nucleotide is preserved. That is to say, the protective group is removed without removing substituents (e.g. functional groups) of the nucleotide.

It is not intended that the method of the present invention be limited to a nucleotide having a particular phosphate group. In one embodiment, said nucleotide comprises a 5'-monophosphate group, more preferably a 5'-diphosphate group, and even more preferably, a 5'-triphosphate group. The present invention also contemplates nucleotides having 5'-polyphosphates consisting of more than three phosphate groups.

It is not intended that the method of the present invention be limited to a specific activated marker molecule. In one embodiment, said activated marker molecule is BODIPY-FL-SE. In another embodiment, said activated marker molecule is Cy5-NHS.

The present invention also contemplates methods of preparing photocleavable marker-polynucleotide conjugates. For example, in one embodiment, the present invention contemplates a method of preparing photocleavable marker-polynucleotide conjugates comprising: a) providing i) an unmodified polynucleic acid, ii) a photocleavable marker nucleotide, and iii) a nucleic acid-modifying enzyme; b) contacting (or mixing or reacting or incubating) said polynucleic acid with said photocleavable marker nucleotide and said modifying enzyme under conditions such that said photocleavable marker nucleotide is incorporated into said polynucleic acid to produce a labeled polynucleic acid. In a preferred embodiment, the method further comprises: c) detecting said incorporated photocleavable marker (or incorporated photocleavable marker-nucleotide) in said labeled polynucleic acid. In one embodiment, the method further comprises (prior to step c): separating unincorporated photocleavable marker nucleotide from said labeled polynucleic acid. Optionally, the method may further comprise the step of removing the incorporated photocleavable marker from said labeled polynucleic acid by exposing said labeled polynucleic acid to electromagnetic radiation, thereby creating treated polynucleic acid.

The present invention also contemplates the above method of preparing a photocleavable marker-polynucleotide conjugate comprising an additional step of subjecting said treated polynucleic acid to a subsequent labeling reaction with a different photocleavable marker nucleotide after said removing step. The present invention also contemplates the above method of preparing a photocleavable marker-polynucleotide conjugate wherein said contacting is performed in the presence of a template selected from the group consisting of polynucleic acid, DNA, RNA, cDNA, oligonucleotides.

It is not intended that the method of preparing a photocleavable marker-polynucleotide conjugate of the present invention be limited to any specific nucleic acid-modifying enzyme. In one embodiment, said nucleic acid-modifying enzyme is a DNA polymerase. In another embodiment, said nucleic acid-modifying enzyme is an RNA polymerase. In a preferred embodiment, said nucleic acid-modifying enzyme is terminal deoxynucleotidyl transferase.

It is not intended that the method of preparing a photocleavable marker-polynucleotide conjugate of the present invention be limited to a particular means by which said incorporated photocleavable marker nucleotide on said polynucleic acid is detected. In one embodiment, said incorporated photocleavable marker nucleotide on said polynucleic acid is detected by a means selected from the group consisting of luminescence, fluorescence, chemiluminescence and mass spectrometry.

It is not intended that the method of preparing a photocleavable marker-polynucleotide conjugate of the present invention be limited to the use of a single photocleavable marker nucleotide. In one embodiment, a plurality of photocleavable marker nucleotides is provided, each of said photocleavable marker nucleotides having a different marker molecule capable of being independently detected.

It is not intended that the method of preparing a photocleavable marker-polynucleotide conjugate of the present invention be limited to the use of a photocleavable marker nucleotide comprising a particular phosphate group. In one embodiment, said photocleavable marker nucleotide is a nucleotide 5'-monophosphate, more preferably a nucleotide 5'-diphosphate, and even more preferably, a nucleotide 5'-triphosphate. The present invention also contemplates photocleavable marker nucleotides having 5'-polyphosphates consisting of more than three phosphate groups.

DEFINITIONS

Unless defined otherwise, all technical and scientific terms used herein have the same meaning as commonly understood by one of ordinary skill in the art. Although any methods and materials similar or equivalent to those described herein can be used in the practice or testing of the present invention, the preferred methods and materials are described. For purposes of the present invention, the following terms are defined below.

As used herein, the term "marker" refers to any atom or molecule which can be used to provide a detectable (preferably quantifiable) signal, and which can be attached to a nucleotides, polynucleotides, or nucleic acids (including polynucleic acids). Markers may provide signals detectable by fluorescence, radioactivity, colorimetry, gravimetry, X-ray diffraction or absorption, magnetism, enzymatic activity, and the like. Such markers can be added to the nucleotides and polynucleotides of the present invention. Marker molecules are "capable of being independently detected" where, in a mixture comprising two or more different markers, each marker has a separate and distinct detectable (preferably quantifiable) signal. For example, the present invention contemplates a photocleavable marker-polynucleotide conjugates comprising a plurality of different photocleavable marker molecules wherein each molecule emits a distinct signal only at a specific wavelength of UV light.

Various methods of adding markers to nucleotides, polynucleotides, or nucleic acids are known in the art and may be used. Examples of markers for nucleotides, polynucleotides, or nucleic acids include, but are not limited to, the following: radioisotopes (e.g. $^3H$), fluorescent markers (e.g. BODIPY, Cy5, Cy3, FITC, rhodamine, and lanthanide phosphors), enzymatic markers (e.g. horseradish peroxidase, beta-galactosidase, luciferase, alkaline phosphatase), biotinyl groups, pre-determined polypeptide epitopes recognized by a secondary reporter (e.g. leucine zipper pair sequences, binding sites for secondary antibodies, metal binding domains, and epitope tags). In some embodiments, markers are attached by linkers, or spacer arms, of various lengths to reduce potential steric hindrance.

Figure 3:
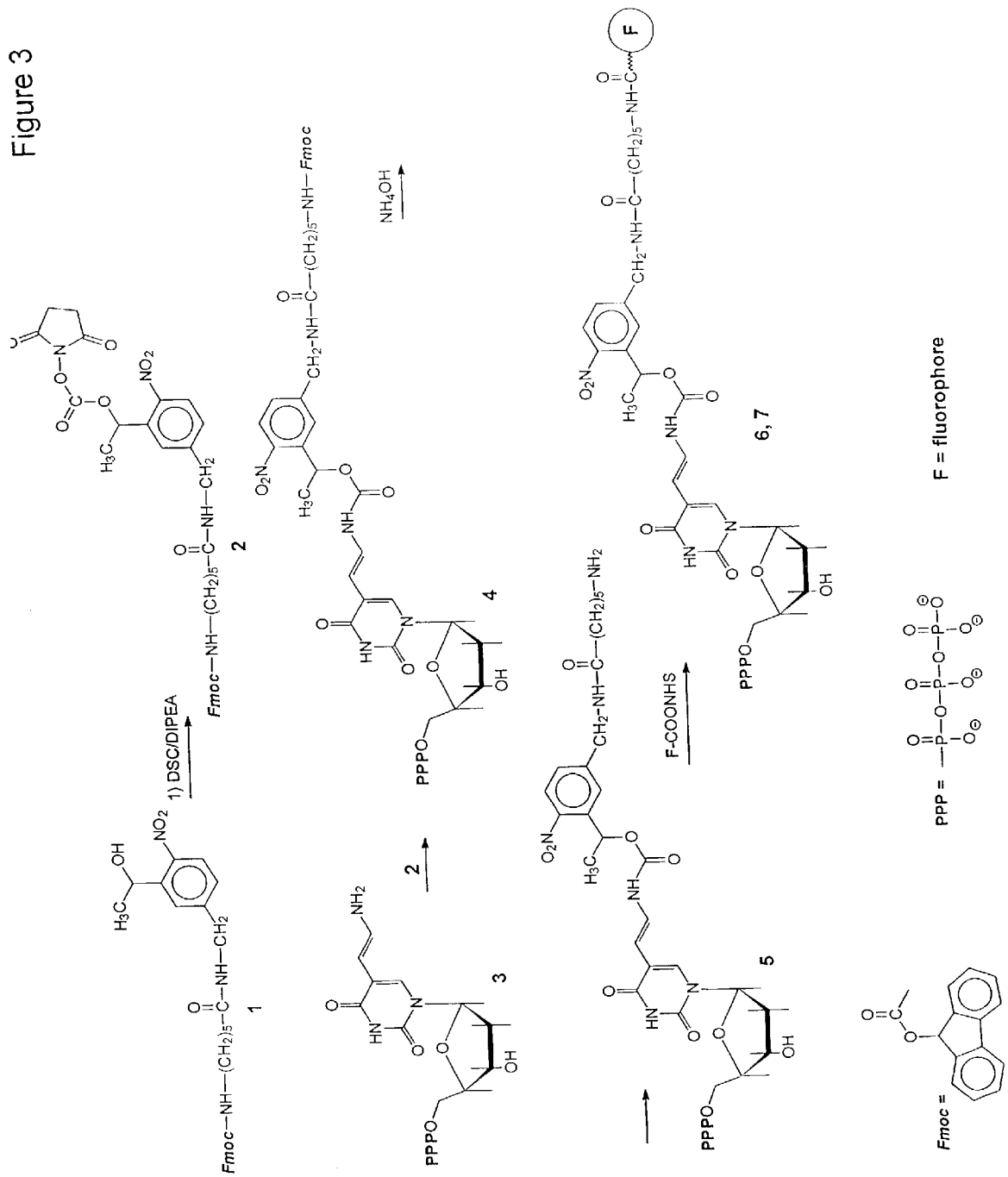
FIG. 3 depicts one example of a synthesis scheme for BODIPY-FL-PC-aadUTP (compound 6) and Cy5-PC-aadUTP (compound 7).

As used herein, the term "photocleavable marker" refers to a marker that may be removed from a nucleotide, polynucleotide, chemical group, or nucleic acid, to which it is attached or operably linked, by exposure to electromagnetic radiation (e.g. visible light, UV light, etc.). The wavelength of light necessary to photocleave the marker is dependent upon the structure of the photocleavable marker used. The present invention contemplates compositions comprising photocleavable markers that are chemical compounds containing a 2-nitrobenzyl moiety such as, for example, compounds 6 & 7 as depicted in FIG. 3, and N-hydroxysuccinimidyl-4-azidosalicyclic acid (NHS-ASA). The terms "photocleavable marker-nucleotide" and "photocleavable marker-nucleotide conjugate" refer to compounds comprising a photocleavable marker that is operably linked to a nucleotide or polynucleotide group. The term "plurality of photocleavable marker nucleotides" as used herein designates that more than one such marker nucleotide is utilized, wherein said plurality comprises two or more different photocleavable marker nucleotides.

As used herein, the term "chelator" refers to a ligand that contains two or more atoms, each of which can simultaneously form a two-electron donor bond (i.e. chelate) to the same metal ion. A "chelator" may also be referred to as a polydentate ligand.

As used herein, the phrase "the photocleavable marker is a chelator capable of forming luminescent complexes," refers to a photocleavable marker molecule comprising a portion that chelates a metal ion (e.g. Terbium, Europium, Samarium, Ruthenium, Calcium, Magnesium, Manganese, Iron, Copper, Cobalt, Nickel, or other polyvalent cations) wherein the chelating of said metal ion allows detection by luminescence. For example, the present invention contemplates a photocleavable marker that is a first chelator (e.g. salicylic acid) capable of forming luminescent complex when reacted with a second chelator (e.g. EDTA) and a metal ion (e.g. $Tb^{3+}$).

As used herein, the term "binding member" refers to a portion of a marker molecule that is operably linked to a nucleotide molecule wherein said marker molecule further binds to another portion of a marker molecule so as to allow detection. For example, the present invention contemplates the detection of a photocleavable marker comprising a first binding member (e.g. biotin) that is detected by binding with a second binding member (e.g. streptavidin). In another example, the present invention contemplates the detection of a photocleavable marker comprising a first binding member (e.g. phenyldiboronic acid) that is detected by binding with a second binding member (e.g. salicylhydroxamic acid).

As used herein, the term "BODIPY-FL" refers to a chemical compound (4,4-difluoro-5,7-dimethyl-4-bora-3a, 4a-diaza-s-indacene-3-propionic acid) that is fluorescent marker having the following chemical structure:

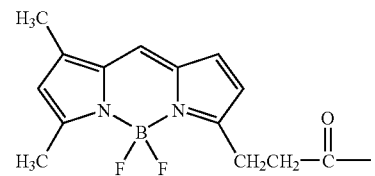

The term BODIPY-FL-SE refers to the succinimidyl ester of BODIPY-FL. The term BODIPY-FL-PC-aadUTP refers to BODIPY-FL that is operably linked to 5-(3-aminoallyl)-2'-deoxyuridine 5'-triphosphate (aadUTP) via a photocleavable linker.

As used herein, the term "Cy5" refers to a chemical compound that is fluorescent marker having the following chemical structure:

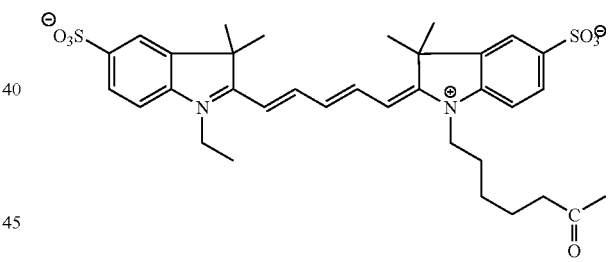

"Cy5" also refers to the chemical compound 1[epsilon carboxy pentyl]1'ethyl 3,3,3',3'-tetramethylindocarbocyanine 5,5'-disulfonate potassium salt N-hydroxysuccinamide ester.

As used herein, the term "photocleavable linker" refers to any chemical group that attaches or operably links a (photocleavable) marker to the nucleobase moiety of a nucleotide, polynucleotide, or nucleic acid. The present invention contemplates photocleavable linkers including, but not limited to, 2-nitrobenzyl moieties, alpha-substituted 2-nitrobenzyl moieties [e.g. 1-(2-nitrophenyl)ethyl moieties], 3,5-dimethoxybenzyl moieties, thiohydroxamic acid, 7-nitroindoline moieties, 9-phenylxanthyl moieties, benzoin moieties, hydroxyphenacyl moieties, and NHS-ASA moieties. The present invention also contemplates photocleavable linkers comprising 2-nitrobenzyl moieties and "cross-linker arms" (or "spacer arms") that further separate a photocleavable marker from the nucleobase moiety of a nucleotide, polynucleotide, or nucleic acid to which it is to be operably linked. Examples of such "cross-linker arms" include, but are not limited to, long alkyl chains or repeat units of caproyl moieties linked via amide linkages.

As used herein, the term "protective group" refers to a chemical group (e.g. Fmoc and Bpoc) which is bound to a monomer unit and which may be selectively removed therefrom to expose an reactive or active site such as, in the specific example of a nucleotide or photocleavable linker, an amine group. The present invention contemplates using protective groups to enable (1) the sequential coupling of a photocleavable linker and a marker molecule, and (2) to prevent the reaction of an activated photocleavable linker with itself. The present invention contemplates, as depicted in FIG. 3 for example, that upon treatment of compound 4 with ammonium hydroxide, the protective group is removed (e.g. compound 5), thus allowing the directed interaction of the succinimidyl ester portion (i.e. the reactive site) of an actived marker molecule with the exposed reactive site of a photocleavable linker to form a photocleavable marker nucleotide or moiety (e.g. compounds 6 & 7).

As used herein, the term "reactive site" refers to the portion of a molecule or chemical group (or moiety) which is available to bind, operably link to, contact, or otherwise interact with another molecule or chemical group after the removal of a protective group. The present invention contemplates photocleavable linkers that comprise a reactive site upon the removal of a protective group such as Fmoc or Bpoc.

As used herein, the term monomer refers to a member of the set of small molecules which are or can be joined together to form a polymer. The set of monomers includes but is not restricted to, for example, the set of nucleotides and the set of pentoses and hexoses. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as nucleotides (including photocleavable marker nucleotides), but could readily be applied in the preparation of other polymers. Such polymers include, for example, both linear and cyclic polymers of nucleic acids.

As used herein, the term "polynucleic acid" refers to both linear and cyclic polymers of nucleic acids. An "unmodified polynucleic acid" refers to naturally occurring polynucleic acids. A "labeled polynucleic acid" refers to a polynucleic acid comprising a marker moiety.

As used herein, the term "template" refers to a nucleic acid molecule which may comprise single- or double-stranded DNA, RNA, or an oligonucleotide. The present invention contemplates the incorporation of photocleavable-marker nucleotides into such templates for various purposes including but not limited to nucleic acid sequencing.

As used herein, the term "nucleic acid-modifying enzyme" refers to an enzyme capable of modifying nucleic acids, nucleotides and polynucleotides. Examples of such enzymes are well known in the art and include methylases (e.g. dam methylase), ligases (e.g. T4 DNA and RNA ligase), nucleases (e.g. Exonuclease III and Mung Bean nuclease), and kinases (e.g. T4 Polynucleotide kinase and Uracil-DNA glycosylase). The term also refers to nucleic acid polymerase such as RNA polymerases (e.g. T7 and SP6 RNA polymerase) and DNA polymerases (e.g. Terminal deoxynucleotidyl transferase, T4 and T7 DNA polymerase, thermophillic DNA polymerases, reverse transcriptases, DNA polymerase I, and DNA polymerase I Klenow fragment).

As used herein, the term "operably linked" refers to the linkage of a chemical group or moiety (e.g. fluorophores, markers, and linkers) to a nucleotide in such a manner that a bond that is capable of being photocleaved is produced. The term also refers to the linkage of phosphate groups to a nucleotide in such a manner so that a nucleotide phosphate (e.g. nucleotide 5' mono- or polyphosphate is produced. In either case, said nucleotide can be a single nucleotide, or a polynucleotide. The term "operably linking" refers to the act of creating an operably linked molecule, moiety or chemical group. The present invention contemplates, for example, phosphate groups, photocleavable linkers and markers that are operably linked to nucleotides. The photocleavable agents of the present invention can be "operably linked" or "incorporated" into nucleotides and nucleic acids. By use of the term "operably linked" or "incorporated" it is not meant that the entire photocleavable marker need be part of the final molecule. Some photocleavable agents of the present invention have reactive groups (i.e. the marker is an "activated marker") and leaving groups such that the photocleavable marker upon incorporation or operable linkage may lose one or more groups.

As used herein, the term "sugar moiety" refers to the sugar molecule or group that is part of a nucleotide. For example, the present invention contemplates nucleotides comprising sugar moiety such as ribose and deoxyribose. The present invention also contemplates "analogs" of said sugar moieties such as dideoxyribose, and 2-fluoro-, 2-methoxy-, and acyclic sugar moiety analogs.

As used herein, the term "nucleobase" refers to a purine or pyrimidine base attached to a 1'-carbon atom of a sugar moiety by an N-glycosidic bond to form a nucleoside. The present invention contemplates such nucleobases as adenine, guanine, cytosine, thymine, and uracil, and analogs thereof such as acyclic nucleobases and any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N-6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N-6-methyladenine, 7-methylguanine, 5-methylaminomethyluracil, 5-methoxyaminomethyl-2-thiouracil, β-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleoside" refers to natural purinic and pyrimidinic nucleobases bound to sugar moieties. For example, the present invention contemplates nucleosides such as adenosine, cytidine, guanosine and uridine (i.e. for RNA) and deoxyadenosine, deoxycytidine, deoxyguanosine, and deoxythymidine (i.e. for DNA). The term "nucleoside analogs" or refers to modified purinic and pyrimidinic nucleobases bound to sugar moieties such as 5-bromodeoxyuridine, deoxyinosine, deoxyuridine, 5-fluorodeoxyuridine, 5-iododeoxyuridine, 5-methyldeoxycytidine, 3'-O-methylguanosine, 7-deaza-2'-deoxyadenosine and deoxyguanosine, and 2'-O-methyl-adenosine, cytidine, guanosine, inosine and uridine. Nucleosides that are bound to one (i.e. a monophosphate) or a plurality (i.e. a di-, tri- or polyphosphate) of phosphate groups are referred to as "Nucleotides." Examples of nucleotides contemplated by the present invention include (but are not limited to): 2'-deoxyuridine 5'-triphosphate (dUTP), 2'-deoxycytidine 5'-triphosphate (dCTP), 2'-deoxyadenosine 5'-triphosphate (dATP), 2'-deoxyguanosine 5'-triphosphate (dGTP), 2'-deoxyinosine 5'-triphosphate (dITP), and 2'-deoxythymidine 5'-triphosphate (dTTP); and 2',3'-dideoxyuridine 5'-triphosphate (ddUTP), 2',3'dideoxyadenosine 5'-triphosphate (ddATP), 2',3'-dideoxycytidine 5'-triphosphate (ddCTP), 2',3'dideoxyguanosine 5'-triphosphate (ddGTP), 2',3'dideoxyinosine 5'-triphosphate (ddITP), and 2',3'dideoxythymidine 5'-triphosphate (ddTTP), and nucleotide analogs. The term "nucleotide analogs" refers to nucleotides which comprise various nucleoside analogs (e.g. 5-fluorodeoxyuridine triphosphate, 5-iododeoxyuridine triphosphate, 5-methyldeoxycytidine triphosphate, 3'-O-methylguanosine triphosphate, 7-deaza-2'-deoxyadenosine and deoxyguanosine triphosphate, and 2'-O-methyl-adenosine, cytidine, guanosine, inosine and uridine triphosphate.

DESCRIPTION OF THE INVENTION

The present invention generally relates to nucleotides and polynucleotides useful in the sequencing of nucleic acids. The present invention specifically relates to compositions comprising nucleotides and polynucleotides comprising photocleavable markers. Such markers are useful in DNA sequencing such as automated DNA sequencing employing fluorescent markers, various forms of parallel sequencing such as sequencing by hybridization (see, e.g., Drmanac et al., (1998) *Nature Biotechnol.*, 16, 54–58), pyrosequencing (see, e.g., Ronaghi et al., (1998) Science, 281, 363–365) and in situ replica amplification. (See, e.g, R D Mitra and G M Church, "In situ localized amplification and contact replication of many individual DNA molecules," *Nucl. Acids Res.*, 27(4): i–vi (1999); Published PCT Patent Application Nos. WO 99/19341 and WO 00/53812 to Church & Mitra).

The compositions and methods of the present invention provide advantages over those of the prior art it that the complex and time-consuming chemical methylation and enzymatic cleavage steps inherent in such methods are eliminated in favor of a rapid and simple photocleavage step.

I. Compositions of the Present Invention

Figure 1:
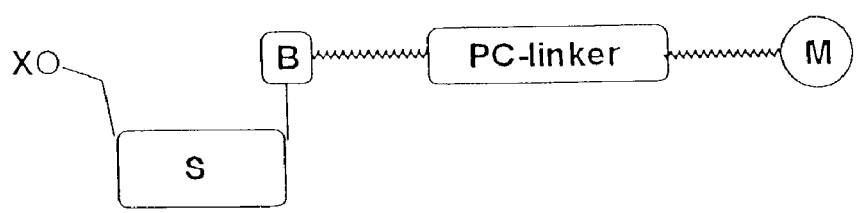
FIG. 1 depicts one example of the general structure of the photocleavable marker-nucleotide conjugates of the present invention, compounds of general formula (I), wherein X is selected from the group consisting of a phosphate group and a hydrogen atom, M is a photocleavable marker, B is a nucleobase, and S is a sugar moiety.
Figure 1:
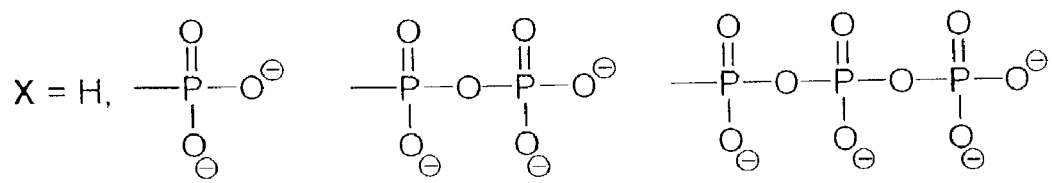

The present invention relates to compositions comprising nucleotides and polynucleotides comprising photocleavable markers. Specifically, the present invention contemplates compositions comprising photocleavable marker-polynucleotide conjugate compounds having the general formula (I), as depicted in FIG. 1, wherein X is selected from the group consisting of a phosphate group and a hydrogen atom, M is a photocleavable marker, B is a nucleobase, PC-linker is a photocleavable linker, and S is a sugar moiety.

It is not intended that the compounds of general formula (I) be limited to a specific phosphate group. In one embodiment, said phosphate group is a monophosphate group, more preferably a polyphosphate (such as a diphosphate group), and even more preferably a triphosphate group. In another embodiment, said phosphate group is a pyrophosphate group.

It is not intended that the nucleobase of the compounds of general formula (I) be limited to a specific nucleobase. In one embodiment, said nucleobase is selected from the group consisting of adenine, cytosine, guanine, thymine, uracil, and analogs thereof.

It is not intended that the sugar moiety of the compounds of general formula (I) be limited to a specific sugar moiety. In one embodiment, said sugar moiety selected from the group consisting of ribose, deoxyribose, dideoxyribose, and analogs thereof, such as, for example, acyclic sugar moieties. (See, e.g., U.S. Pat. No. 5,558,991 to Trainor et al., "DNA Sequencing Method Using Acyclonucleoside Triphosphates").

It is not intended that the photocleavable linker of the compounds of general formula (I) be limited to a specific photocleavable linker. In one embodiment, said photocleavable linker is a photocleavable linker comprising a protective group selected from the group consisting of 9-fluorenylmethoxycarbonyl (Fmoc) and 2-(4-biphenyl)propyl(2) oxycarbonyl (Bpoc), and derivatives thereof (e.g. 9-fluorenylmethoxycarbonyl N-hydroxysuccinimidyl ester; Fmoc-NHS).

Figure 4:
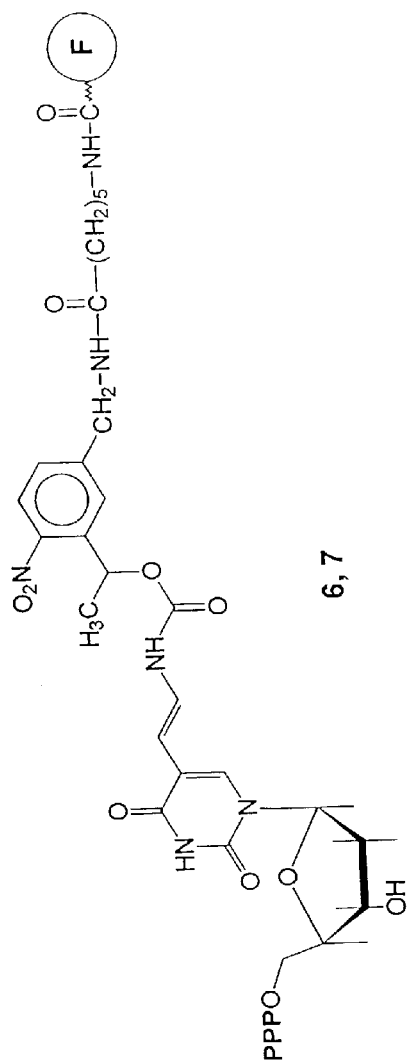
FIG. 4 depicts the chemical structures of BODIPY-FL-PC-aadUTP (compound 6) and Cy5-PC-aadUTP (compound 7)
Figure 4:
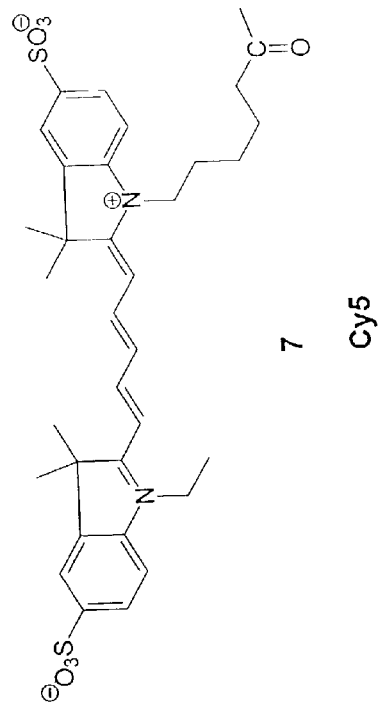
Figure 4:
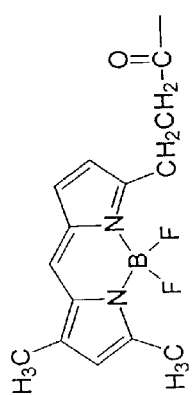
Figure 4:
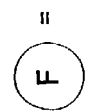
Figure 4:
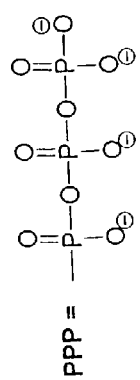
Figure 5:
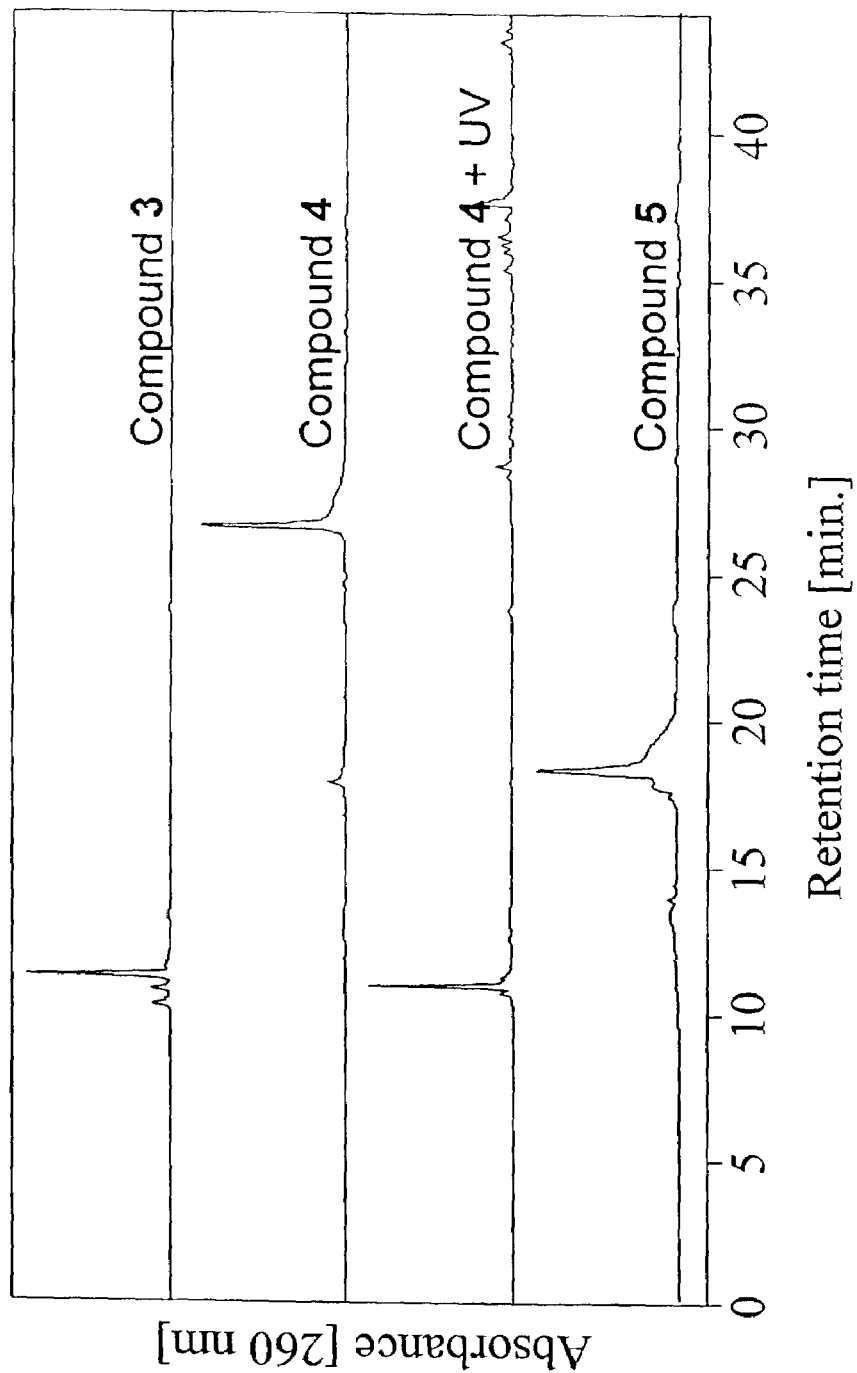
FIG. 5 shows the results of the high performance liquid chromatography (HPLC) starting material (compound 3), compound 4, compound 4 after UV illumination, and compound 5. Note that the retention time of compound 4 (after illumination) regenerates the starting material as expected.

It is not intended that the compounds of general formula (I) be limited to any specific photocleavable marker. In one embodiment, said photocleavable marker is BODIPY-FL (FIG. 4) or its succinimidyl ester, BODIPY-FL-SE. In another embodiment, said photocleavable marker is Cy5, or its succinimidyl ester, Cy5-NHS. (FIG. 4). Succinimidyl esters are preferred for the conjugation of dyes to nucleotides because they form a very stable amide bond between the dye and the nucleotide. The present invention also contemplates the use of other marker (or labels) such as tetramethylrhodamine (6-TAMRA), fluorescein (5-FAM), rhodamine X (6-ROX), and 2',7'-dimethoxy-4',5'-dichlorofluorescein (6-JOE). Additional markers useful in conjunction with the present invention are shown in Table 1. For DNA sequencing applications, photocleavable markers comprising BODIPY moieties are useful because they are isomerically pure and cause little perturbation to the mobility of DNA fragments during polyacrylamide gel electrophoresis.

Figure 12:
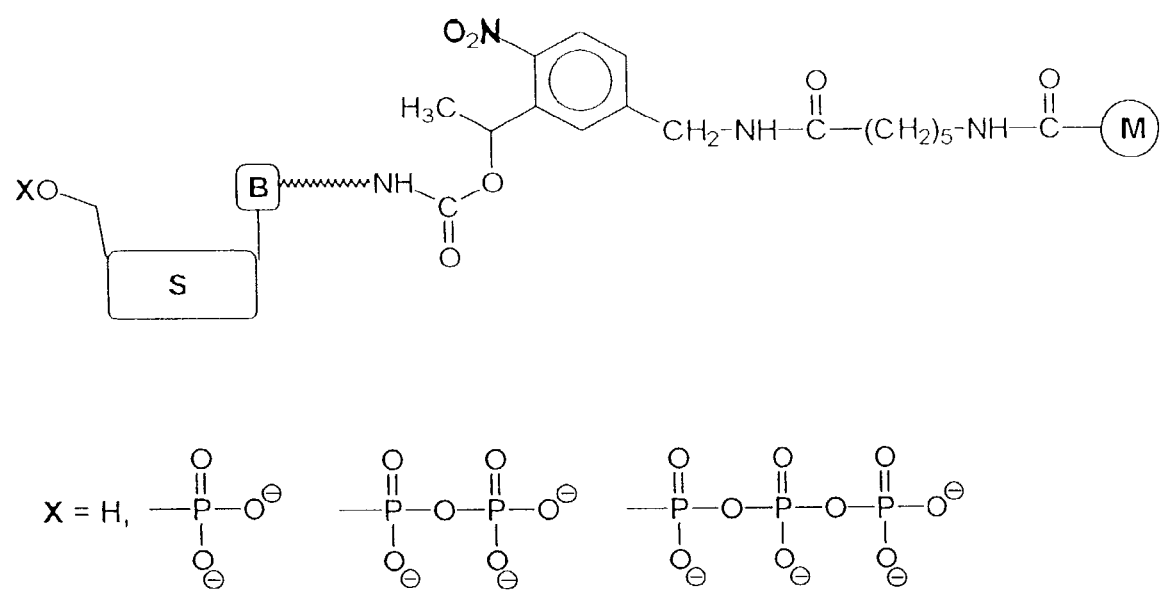
FIG. 12 depicts one example of the compounds of general formula (II) wherein X is selected from the group consisting of a phosphate group and a hydrogen atom, M is a photocleavable marker, B is a nucleobase, and S is a sugar moiety.
Figure 13:
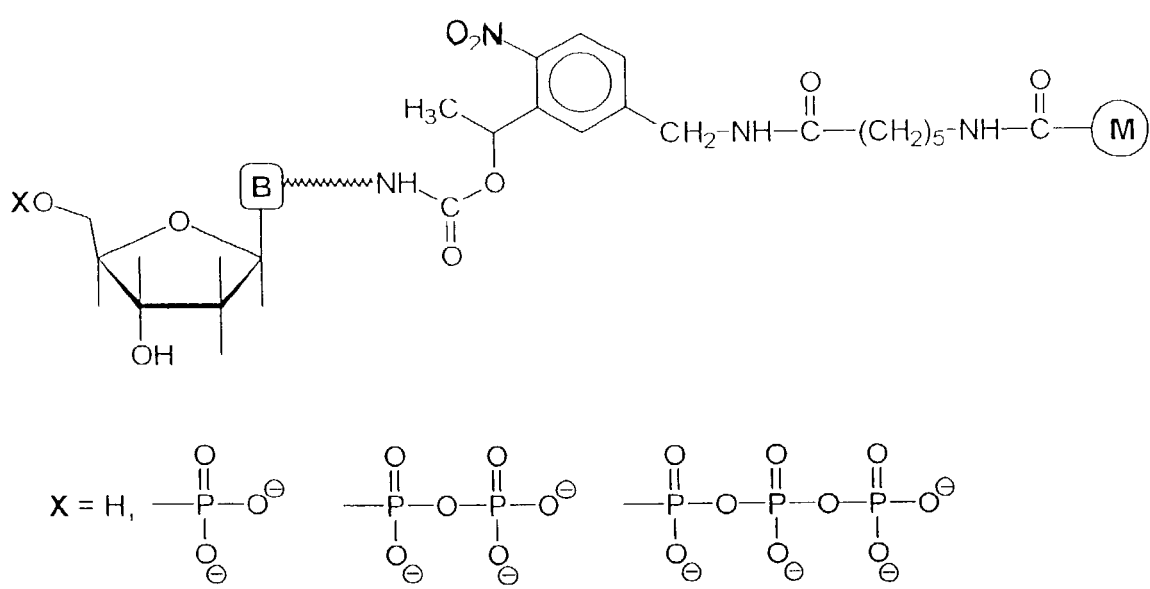
FIG. 13 depicts a further example of the compounds of general formula (II), as described in FIG. 12, wherein the sugar moiety is a deoxyribose.

The present invention also contemplates compositions comprising photocleavable marker-polynucleotide conjugate compounds having the general formula (II) (as depicted in FIG. 12), wherein X is selected from the group consisting of a phosphate group and a hydrogen atom, M is a photocleavable marker, B is a nucleobase, and S is a sugar moiety.

It is not intended that the compounds of general formula (II) be limited to a specific phosphate group. In one embodiment, said phosphate group is a monophosphate group, more preferably a polyphosphate (such as a diphosphate group), and even more preferably a triphosphate group. In another embodiment, said phosphate group is a pyrophosphate group.

It is not intended that the nucleobase of the compounds of general formula (II) be limited to a specific nucleobase. In one embodiment, said nucleobase is selected from the group consisting of adenine, cytosine, guanine, thymine, uracil, and analogs thereof.

It is not intended that the sugar moiety of the compounds of general formula (II) be limited to a specific sugar moiety. In one embodiment, said sugar moiety selected from the group consisting of ribose, deoxyribose, dideoxyribose, and analogs thereof, such as, for example, acyclic sugar moieties. (See, e.g., U.S. Pat. No. 5,558,991 to Trainor et al., "DNA Sequencing Method Using Acyclonucleoside Triphosphates").

It is not intended that the photocleavable linker of the compounds of general formula (II) be limited to a specific photocleavable linker. In one embodiment, said photocleavable linker is a photocleavable linker comprising a protective group selected from the group consisting of 9-fluorenylmethoxycarbonyl (Fmoc) and 2-(4-biphenyl)propyl(2)oxycarbonyl (Bpoc), and derivatives thereof (e.g. 9-fluorenylmethoxycarbonyl N-hydroxysuccinimidyl ester; Fmoc-NHS).

It is not intended that the compounds of general formula (II) be limited to any specific photocleavable marker. In one embodiment, said photocleavable marker is BODIPY-FL (FIG. 4) or its succinimidyl ester, BODIPY-FL-SE. In another embodiment, said photocleavable marker is Cy5, or its succinimidyl ester, Cy5-NHS. (FIG. 4). Succinimidyl esters are preferred for the conjugation of dyes to nucleotides because they form a very stable amide bond between the dye and the nucleotide. The present invention also contemplates the use of other marker (or labels) such as tetramethylrhodamine (6-TAMRA), fluorescein (5-FAM), rhodamine X (6-ROX), and 2',7'-dimethoxy-4',5'-dichlorofluorescein (6-JOE). For DNA sequencing applications, photocleavable markers comprising BODIPY moieties are useful because they are isomerically pure and cause little perturbation to the mobility of DNA fragments during polyacrylamide gel electrophoresis. Additional markers useful in conjunction with the present invention are shown in Table 1.

One example of the photocleavable markers found in the compounds of general formulas (I) & (II) contemplated by the present invention are chemical compounds which contain, or are operably linked to, a 2-nitrobenzyl moiety. (See, e.g., U.S. Pat. Nos. 5,922,858 & 5,643,722 to Rothschild et al.). Upon illumination, these aromatic nitro compounds undergo an internal oxidation-reduction reaction (V. N. Rajasekharan Pillai, "Photoremovable Protecting Groups in Organic Synthesis," *Synthesis,* 1: 1–26 (1980); Patchornik et al., (1970) *J. Am. Chem. Soc.* 92: 6333–35). As a result, the nitro group is reduced to a nitroso group and an oxygen is inserted into the benzylic carbon-hydrogen bond at the ortho position. The primary photochemical process is the intramolecular hydrogen abstraction by the excited nitro group. This is followed by an electron-redistribution process to the aci-nitro form which rearranges to the nitroso product. Subsequent thermal reaction leads to the cleavage of substrate from the nitrobenzyl linkage. Examples of photocleavable markers of the present invention are shown in FIG. 4.

TABLE 1

| Name and Molecular weight | Formula | Fluorescence Properties |
|---|---|---|
| BODIPY-FL, SSE M. WT. 491 | | Excitation = 502 nm Emmision = 510 nm Extinction = 75,000 |
| NBD M. WT. 391 | | Excitation = 466 nm Emmision = 535 nm Extinction = 22,000 |
| Bodipy-TMR-X, SE M. WT. 608 | | Excitation = 544 nm Emmision = 570 nm Extinction = 56,000 |

TABLE 1-continued

| Name and Molecular weight | Formula | Fluorescence Properties |
|---|---|---|
| Bodipy-R6G M. WT. 437 | | Excitation = 528 nm Emmision = 547 nm Extinction = 70,000 |
| Fluorescein (FAM) M. WT. 473 | | Excitation = 495 nm Emmision = 520 nm Extinction = 74,000 |
| Fluorescein (SFX) M. WT. 587 | | Excitation = 494 nm Emmision = 520 nm Extinction = 73,000 |
| PyMPO M. WT. 582 | | Excitation = 415 nm Emmision = 570 nm Extinction = 26,000 |
| 5/6-TAMRA M. WT. 528 | | Excitation = 546 nm Emmision = 576 nm Extinction = 95,000 |

In another embodiment, the compounds of general formulas (I) & (II) are chemical compounds which contain, or are operably linked to a photocleavable linker selected from the group consisting of alpha-substituted 2-nitrobenzyl moieties [e.g. 1-(2-nitrophenyl)ethyl moieties], 3,5-dimethoxybenzyl moieties, thiohydroxamic acid, 7-nitroindoline moieties, 9-phenylxanthyl moieties, benzoin moieties, hydroxyphenacyl moieties, and NHS-ASA moieties.

It may sometimes be desirable to create a distance between the substrate (e.g. such as nucleotides, polynucleotides, oligonucleotides, or nucleic acids) and the photocleavable marker moiety. To accomplish this, photocleavable moieties may be separated from substrates by cross-linker arms. Cross-linkers increase substrate access and stabilize the chemical structure, and can be constructed using. for example, long alkyl chains or multiple repeat units of caproyl moieties linked via amide linkages.

In one embodiment, the marker BODIPY-FL is operably linked to a an alkyl chain cross-linker via the marker's succinimidyl ester group, and said cross-linker is directly attached to a 2-nitrobenzyl moiety linked to a nucleotide moiety. (See FIG. 3, synthesis of compound 6 from compound 5). In another embodiment, the marker Cy5 is operably linked as described above. (See FIG. 3, synthesis of compound 7 from compound 5). Other examples of photocleavable markers include photocleavable coumarin, photocleavable dansyl, photocleavable dinitrophenyl and photocleavable coumarin-biotin.

Photocleavable markers are cleaved by electromagnetic radiation such as UV light. Cleavage of photocleavable markers is dependent on the structure of the photoreactive moiety and the wavelength of electromagnetic radiation used for illumination. Other wavelengths of electromagnetic radiation should not damage nucleotides or other chemical moieties to which the photocleavable marker is bound, attached or operably linked. Typical illumination times vary from less than 1 hour (e.g. 1 minute to thirty minutes) to about 24 hours and radiation or illumination sources are placed within about 10 cm of the reaction mixture (and set on low power so as to minimize side reactions, if any, which may occur).

It is not intended that the photocleavable marker of the compounds of general formulas (I) & (II) be detected by any specific method. In one embodiment, said photocleavable marker is a molecule that can be detected by mass spectrometry. In another embodiment, said photocleavable marker is a fluorescent moiety and can be detected by fluorescence spectroscopy.

In another embodiment, said photocleavable marker is a binding member and is detected via a second binding member. Specifically, the present invention contemplates photocleavable markers wherein a portion of a marker molecule is operably linked to a nucleotide molecule. Said marker molecule is further bound to another portion of a marker molecule so as to allow detection. For example, in one embodiment, the present invention contemplates the detection of a photocleavable marker comprising biotin as a first binding member, that is detected by binding with streptavidin as the second binding member. In another embodiment, said first binding member is phenyldiboronic acid and salicylhydroxamic acid is said second binding member.

In a preferred embodiment, said photocleavable marker is a chelator capable of forming luminescent complexes. In principle, a first chelator is incorporated into a nucleic acid by being operably linked to a photocleavable nucleotide. A second chelator is added free in solution with a metal ion and the luminescent complex is formed. Examples of some of the first and second chelators, and metal ions, contemplated by the present invention are summarized in Table 2 below. The present invention contemplates embodiments wherein said first and second chelators are the same molecule, as well as embodiments in which said first and second chelators are different molecules. (See, e.g., Table 2).

In one embodiment, a first chelator is incorporated into immobilized polynucleotide, followed by the addition of a second chelator and metal ion such that a luminescent complex is formed. Excess (i.e. unbound) second chelator and metal ion are washed away, and said complex is detected by luminescence assay. In another embodiment, said complex is detected in solution by performing a dissociation wherein an excess of a competing chelator (e.g. "BCPDA" or 4,7-bis(chlorosulfophenyl)-1,10-phenantroline-2,9-dicarboxylic acid) and an enhancing agent (such as, for example, a detergent) are added to the first chelator incorporated into an immobilized polynucleotide. (See I. Hemmila, "Applications of Fluorescence in Imunoassays," Wiley-Interscience, New York, 1991).

TABLE 2

| First Chelator | Second Chelator | Metal Ion(s) |
|---|---|---|
| salicylic acid | EDTA | $Tb^{3+}$ |
| 3-hydroxypyridine | 1,10-phenantroline | $Eu^{3+}$ |
| β-diketone (β-naphthoyl-trifluoroacetone) | EDTA | $Tb^{3+}$, $Eu^{3+}$, or $Sm^{3+}$ |
| β-diketone (β-pivaloyl-trifluoroacetone) | EDTA | $Tb^{3+}$ or $Eu^{3+}$ |
| 2,2'-bipyridine | EDTA or 2,2'-bipyridine | $Ru^{3+}$ |

II. Methods of the Present Invention

A. Photocleavable Marker-Polynucleotide Conjugates

Figure 2:
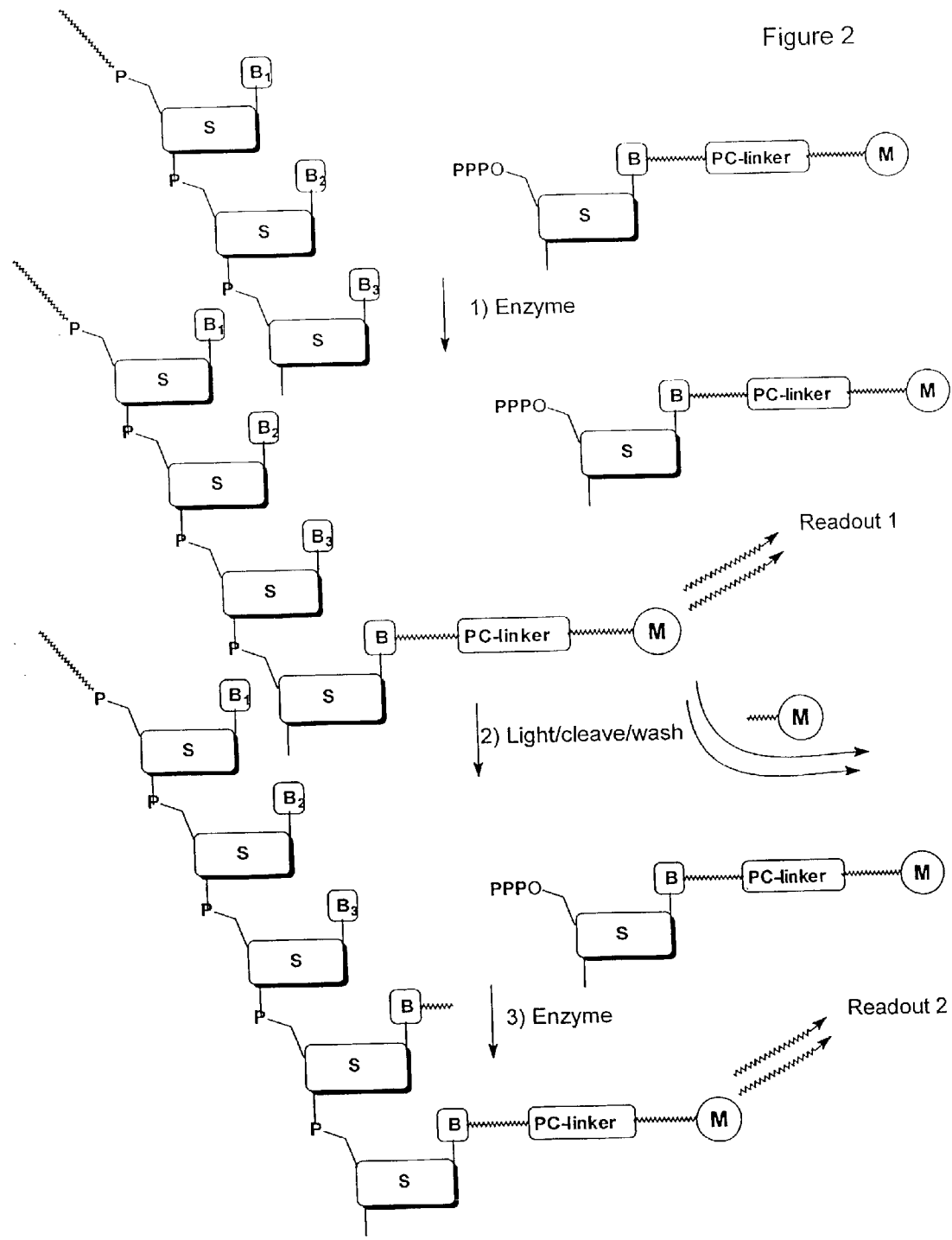
FIG. 2 shows one example of the incorporation of a photocleavable marker-nucleotide conjugate into polynucleic acid, detection of the marker, and removal of the marker by photocleavage, subsequent incorporation of the same (or a different) photocleavable marker-nucleotide conjugate into the same polynucleic acid and its subsequent detection, followed by separation on denaturing polyacrylamide gel and fluorescence imaging.
Figure 8:
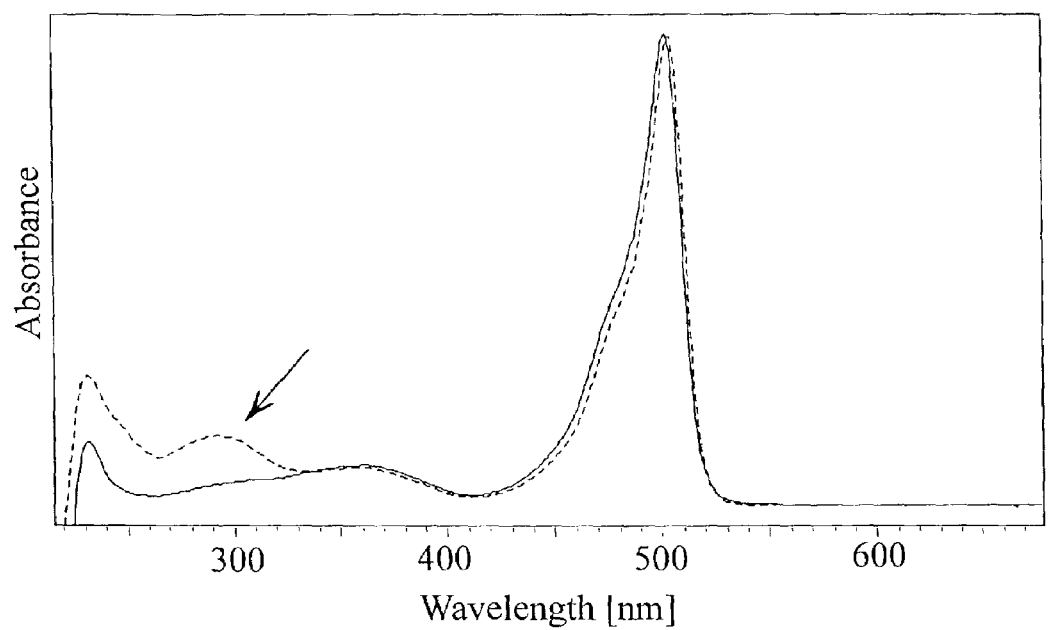
FIG. 8 shows the UV-VIS absorbance spectra of compound 6 (dashed line) compared with that of BODIPY-FL dye (solid line). A characteristic band with a maximum at ~270 nm was observed for compound 6 in addition to fluorophore absorption with a maximum at ~502 nm. This feature is consistent with the presence of amidoallyluridine/2-nitrophenyl-ethyl group.
Figure 9:
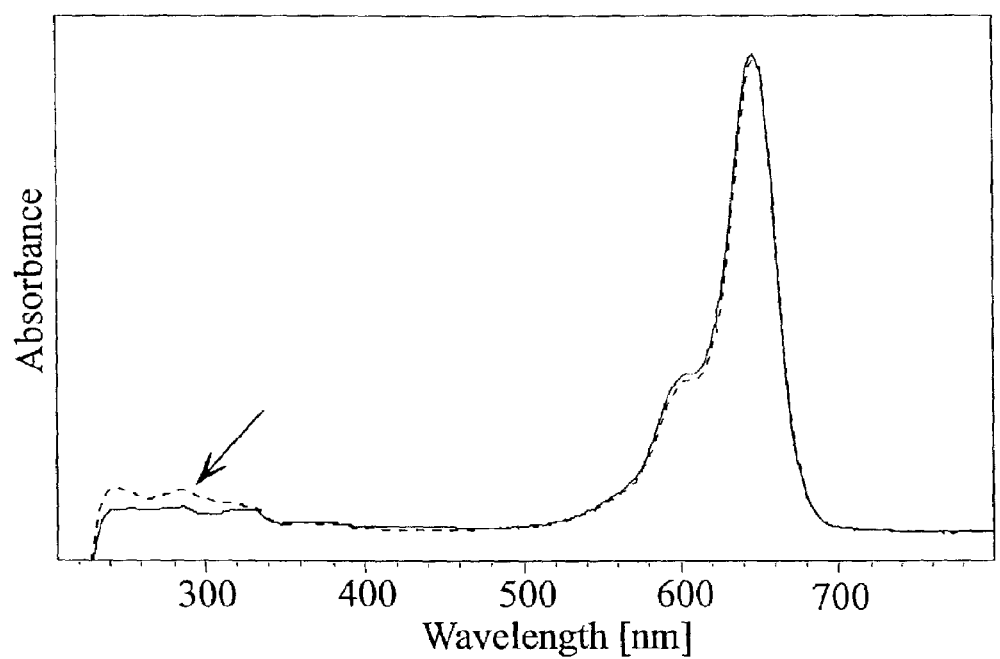
FIG. 9 shows the UV-VIS absorbance spectra of compound 7 (dashed line) compared with that of Cy5 dye (solid line). A characteristic band with a maximum at ~270 run was observed for compound 7 in addition to fluorophore absorption with a maximum at ~650 nm. This feature is consistent with the presence of amidoallyluridine/2-nitrophenyl-ethyl group.

The present invention further relates to the methods of preparing photocleavable marker-polynucleotide conjugates. As depicted in FIG. 2, the overall method of the present invention involves the incorporation of photocleavable marker-nucleotide conjugates into polynucleotides, nucleic acids, polynucleic acids, and other suitable templates. Once incorporated into a polynucleotide or polynucleic acid, the photocleavable marker is detected by such methods as luminescence, fluorescence, chemiluminescence or mass spectrometry. After detection of the photocleavable marker, said marker is removed by photocleavage (e.g. by UV irradiation) and washed away to separate free (i.e. cleaved) marker-nucleotides from the reaction mixture. The entire process is then repeated again with the same photocleavable marker-nucleotide being incorporated into a different position on the same nucleic acid or polynucleic acid, followed by detection of the photocleavable marker, etc. as described above. However, it important to note that the present invention also contemplates embodiments in which different photocleavable marker-nucleotide and nucleotide conjugates are employed in the subsequent incorporation steps of the above process. Such an embodiment employs two or more different marker moieties that can be independently detected (i.e. each marker has a distinct UV-VIS absorbance spectra such that they are distinguishable upon signal detection as contemplated herein). For example, FIG. 8 depicts a comparison of the UV-VIS absorbance spectra for BODIPY-FL dye (~270 nm) and the photocleavable marker-nucleotide, BODIPY-FL-PC-aadUTP (compound 6)(~370 nm). Moreover, FIG. 9 depicts a comparison of the UV-VIS absorbance spectra for Cy5 dye (~270 μm) and the photocleavable marker-nucleotide, Cy5-PC-aadUTP (compound 7)(~650 nm). When taken together, the UV-VIS spectral values indicated in FIGS. 8 and 9 indicate that a method of incorporating a photocleavable marker-nucleotide conjugate into the same polynucleic acid would allow the independent detection of said markers since both photocleavable marker-nucleotide are distinguishable over the fluorophore dyes and starting material (aadUTP) of which they are comprised, as well as, each other.

Figure 10:
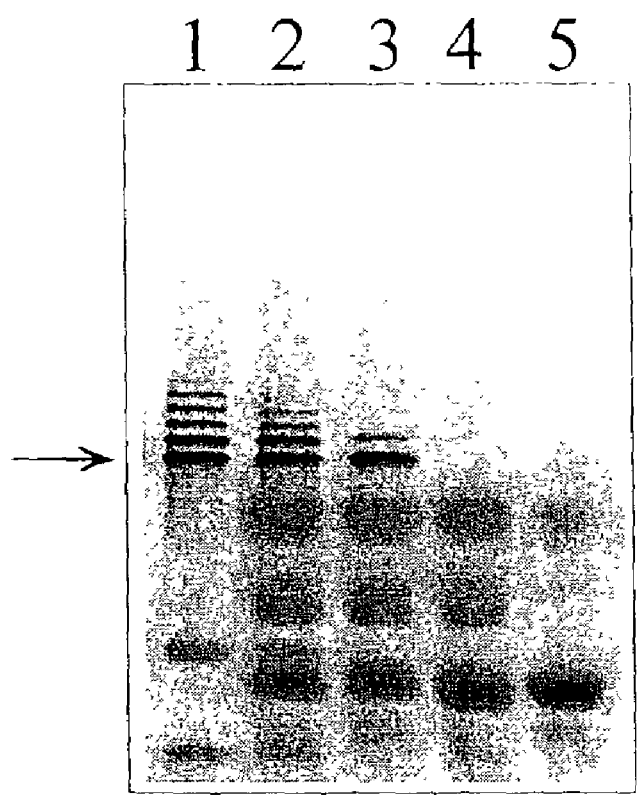
FIG. 10 depicts one example of the incorporation of compound 6 into an oligonucleotide followed by: labeling with fluorescein-11-dUTP (lane 1); labeling with mixture of fluorescein-11-dUTP and compound 6 (BODIPY-FL-PC-dUTP)(lane 2); labeling with BODIPY-FL-PC-dUTP (lane 3); BODIPY-FL-PC-dUTP only (i.e. no DNA)(lane 4); or fluorescein-11-dUTP only (i.e. no DNA)(lane 5).

It is not intended that the present invention be limited to a specific method of incorporating photocleavable marker-nucleotides into polynucleotides, nucleic acids, polynucleic acids, oligonucleotides, and other suitable templates (to form photocleavable marker-polynucleotide conjugates). In one embodiment, said incorporation involves the enzymatic incorporation of the photocleavable marker-nucleotide conjugate BODIPY-FL-PC-aadUTP into an oligonucleotide specific for the human Cystic Fibrosis Transmembrane Regulator Gene using the GeneImages 3' oligolabelling kit (AP-Biotech) (as per the manufacturers instructions) wherein an unmodified polynucleic acid or polynucleotide is incubated with said marker-nucleotide 5' triphosphate conjugate and a DNA or RNA modifying enzyme such as terminal deoxynucleotidyl transferase. In another embodiment, the photocleavable marker-nucleotide conjugate Cy5-PC-aadUTP is incorporated. FIG. 10 depicts an example of such an incorporation of BODIPY-FL-PC-aadUTP into a polynucleic acid or polynucleotide.

It is not intended that the present invention be limited to a specific method of detecting a photocleavable marker-nucleotide conjugate. In one embodiment, said method of detecting is selected from the group consisting of luminescence, fluorescence, chemiluminescence or mass spectrometry. For example, in one embodiment, said photocleavable marker is detected by denaturing polyacrylamide gel electrophoresis followed by fluorescence image scanning before photocleavage has occurred. (See, e.g., FIG. 10). Note that such detection of photocleavable markers may be accomplished before or after photocleavage of the photocleavable marker-nucleotide (or photocleavable marker-polynucleotide conjugate). (See, e.g., FIG. 11).

Figure 6:
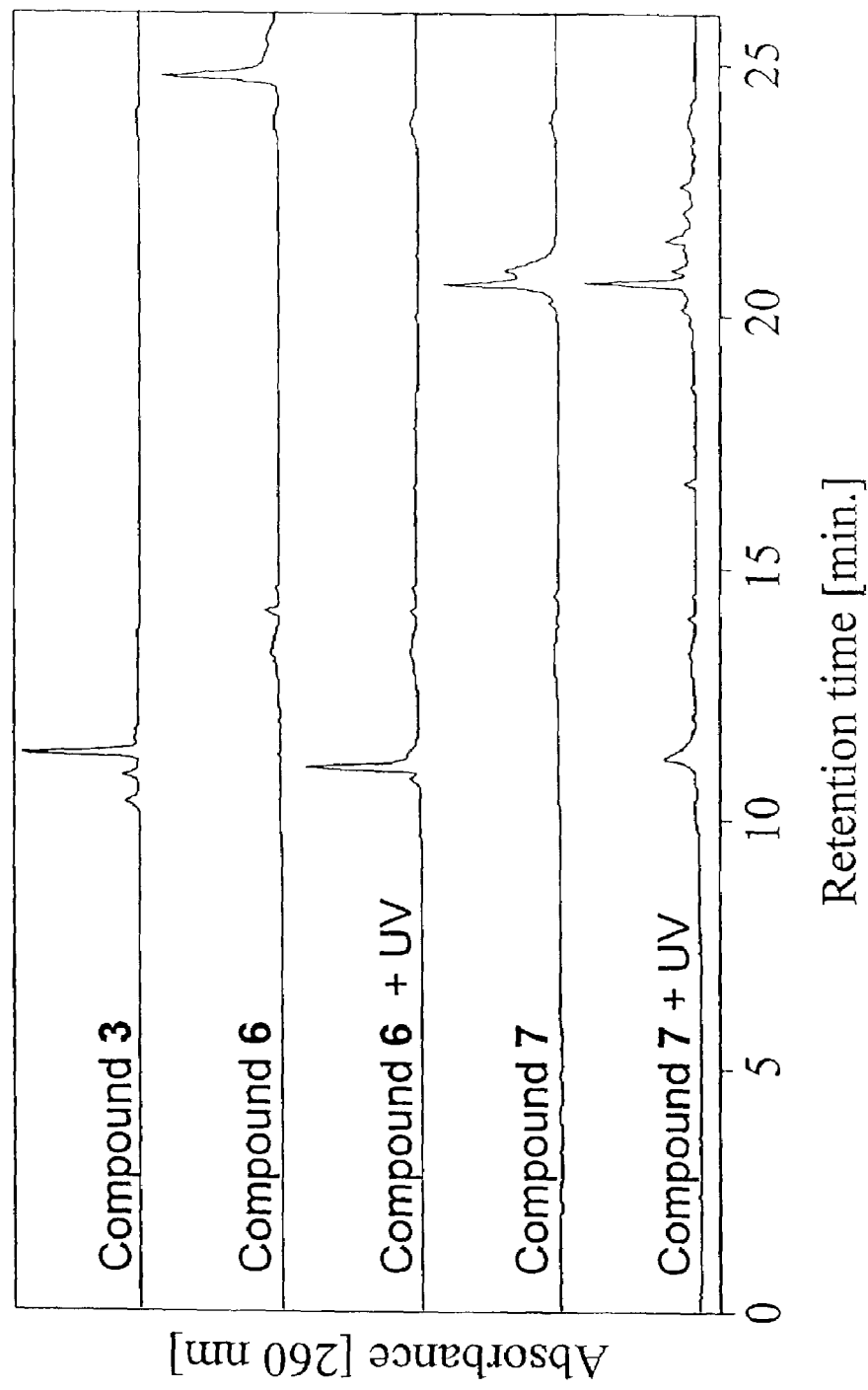
FIG. 6 shows the results of the HPLC of compounds 6 and 7 before and after UV irradiation. Note that after UV illumination, compounds 6 and 7 convert to starting material (compound 3) which shows successful fluorophore removal upon UV exposure.
Figure 7:
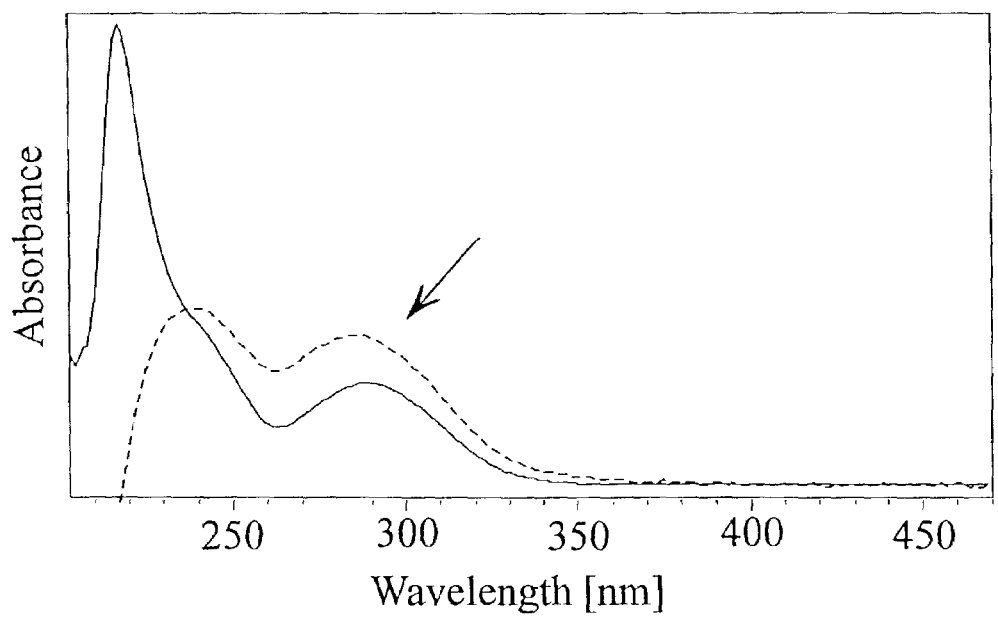
FIG. 7 shows the UV-VIS absorbance spectra of the starting material (compound 3, solid line) compared with that of compound 5 (dashed line). For compound 5, an increase in absorption at ~270 nm was observed with absorption extending towards ~370 nm, as expected.

It is not intended that the present invention be limited to a particular means by which a photocleavable marker is cleaved. For example, in one embodiment, a photocleavable marker comprising BODIPY-FL is cleaved from its nucleotide conjugate after being subjected to irradiation by near UV light (300–365 nm, ~1 mW/cm$^2$) for five minutes. In another embodiment, a photocleavable marker comprising Cy5 is cleaved from its nucleotide conjugate under the same conditions (and in the same manner) as described above. FIG. 6 depicts HPLC chromatograms of photocleavable marker nucleotides of the present invention comprising either BODIPY-FL (compound 6) or Cy5 (compound 7) before and after UV irradiation as described above. FIG. 6 indicates that UV irradiation cleaves the photocleavable moiety from the nucleotide to which it was operably linked with the conversion of compounds 6 & 7 to compound 3 (aadUTP) (i.e. fluorophore removal was successful).

B. Photocleavable Marker-Nucleotide Conjugates

The present invention also relates to the methods of preparing photocleavable marker-nucleotide conjugates. It is not intended that the present invention be limited to a particular method of preparing photocleavable marker-nucleotide conjugates. In one embodiment, a method for the synthesis of a photocleavable marker-nucleotide conjugate comprising a fluorophore selected from the group consisting of BODIPY-FL (i.e. resulting in compound 6) or Cy5 (i.e. resulting in compound 7) is as depicted by the chemical synthesis scheme of FIG. 3.

Briefly, compound 1 comprising the protective group, Fmoc, was prepared as described in Olejnik et al., (1998), Methods Enzymol., 291: 135–54, and reacted in acetonitrile, with N,N-diisopropylethylamine (DIPEA) and N,N'-disuccinimidyl carbonate (DSC) under conditions such that the intermediate compound 2 was formed. Compound 2 purified by chromatography and reacted with an aminoallyl-deoxynucleotide triphosphate (e.g. aadUTP) under conditions such that compound 4 was formed. Compound 4 was purified by reverse phase high performance liquid chromatography (RP-HPLC), and subsequently reacted with ammonia such that the Fmoc protective group was removed and compound 5 was produced. Compound 5 was also purified by RP-HPLC and then incubated with the succinimidyl ester of a fluorophore selected from BODIPY-FL (to make compound 6) or Cy5 (to make compound 7). Compounds 6 & 7 were analyzed by photocleavage and HPLC. (See, e.g., FIGS. 6 & 8).

DESCRIPTION OF PREFERRED EMBODIMENTS

As noted above, the compositions of the present invention are useful in DNA sequencing such as automated DNA sequencing employing fluorescent markers, various forms of parallel sequencing such as sequencing by hybridization. For example, the present invention contemplates the utilization of photocleavable marker-nucleotides in the method to clone and amplify DNA by PCR as taught in R D Mitra and G M Church, "In situ localized amplification and contact replication of many individual DNA molecules," Nucl. Acids Res., 27(4): i–vi (1999), herein incorporated by reference. In Mitra & Church, a method to clone and amplify DNA by performing PCR in a thin polyacrylamide film poured on a glass microscope slide. Id. The polyacrylamide matrix retards the diffusion of the linear DNA molecules so that the amplification products remain localized near their respective templates. Id. At the end of the reaction, a number of PCR colonies have formed, each one "grown" from a single template molecule, with as many as five million clones amplified and sequenced in parallel on a single slide using a sequencing-by-synthesis method such as pyrosequencing. Id. This is usually adequate for gene identification or mini-sequencing. However, a new sequencing-by-synthesis method, fluorescent in situ sequencing extension quantitation (FISSEQ), is particularly suitable. Id.

Briefly, in FISSEQ, the DNA is extended by adding a single type of fluorescently-labeled nucleotide triphosphate to the reaction, followed by the washing away of unincorporated nucleotide, detecting the incorporation of the nucleotide by measuring fluorescence, and repeating the cycle until synchrony is lost. At each cycle, the fluorescence from previous cycles is "bleached" or digitally subtracted, allowing one to deduce the sequence of each polony iteratively. In a preferred embodiment, the present invention contemplates the utilization of the photocleavable marker-nucleotides described herein as a source of fluorescently-labeled nucleotide triphosphates in the FISSEQ method. Said photocleavable marker-nucleotides provide the added advantage over the method of Mitra & Church by allowing a simplified, expedient, non-enzymatic cleavage (i.e. the cleavage of the fluorescent marker of the present invention is by photolysis) of the fluorescent marker moiety from the nucleic acid (or polynucleic acid) into which it was incorporated.

Experimental

The following examples serve to illustrate certain preferred embodiments and aspects of the present invention and are not to be construed as limiting the scope thereof.

In the experimental disclosure which follows, the following abbreviations apply: eq (equivalents); FITC (fluorescein isothiocyanate); M (Molar); µM (micromolar); N (Normal); mol (moles); mmol (millimoles); µmol (micromoles); nmol (nanomoles); g (grams); mg (milligrams); µg (micrograms); ng (nanogram); L (liters); ml (milliliters); µl (microliters); cm (centimeters); mm (millimeters); µm (micrometers); nm (nanometers); ° C. (degrees Centigrade); rpm (revolutions per minute); EDTA (ethylenediaminetetracetic acid); dCTP (2'-deoxycytidine 5'-triphosphate); dUTP (2'-deoxyuridine 5'-triphosphate); Roche Molecular (Roche Molecular Biochemicals, Indianapolis, Ind.); Gibco-BRL (Gibco-BRL Life Technologies, Inc., Rockville, Md.); Molecular Probes (Molecular Probes, Eugene, Oreg.); Sigma (Sigma Chemical Co., St. Louis, Mo.);Promega (Promega Corp., Madison, Wis.); AB (Applied Biosystems, Foster City, Calif.).

EXAMPLE 1

Synthesis of Photocleavable BODIPY-FL Deoxyuridine Triphosphate (BODIPY-FL-PC-aadUTP) (FIG. 3, 4)

In this example, one method for the production of the photocleavable marker-nucleotide conjugate, BODIPY-FL-PC-aadUTP (compound 6), is described.

A. Synthesis of Intermediate Compounds (Compounds 2, & 5)

Compound 1 (Olejnik, J., E. Krzymanska-Olejnik, and K. J. Rothschild. 1998. *Methods Enzymol.* 291:135–54) (100 mg, 0.19 mmol) was dissolved in anhydrous acetonitrile (10 ml) and to this solution 50 µl (0.285 mmol, 1.5 eq.) of N,N-diisopropylethylamine (DIPEA) (Sigma Cat. No. D 3887) was added followed by N,N'-disuccinimidyl carbonate (DSC) (Sigma Cat. No. D 3773) (75 mg, 0.285 mmol, 1.5 eq.). The mixture was stirred at room temperature overnight, volatile compounds removed under reduced pressure and the intermediate (compound 2) purified on a silica gel column using a step (0–1.5%) gradient of MeOH in $CHCl_3$ with a yield of 500 mg (39%).

To make compound 5, 1 mg (1.9 µmol) of 5-(3-aminoallyl)-2-deoxyuridine 5'-triphosphate (compound 3) (aadUTP) (Sigma Cat. No. A 5660) was dissolved in 100 µl of 50 mM $NaHCO_3$ (pH 8.5). To this solution, a solution of 5 mg of compound 2 (7.6 µmol, 4 eq.) in 200 µl of acetonitrile was added. The mixture was incubated at room temperature for 2 hours and purified using preparative RP-HPLC (Waters NovaPak C18, 10×100 mm) using 0–90% gradient of acetonitrile in 50 mM triethylammonium acetate (pH 4.5) over a period of 45 minutes with flow rate 1 ml/min. The fractions containing compound 4 were pooled and freeze dried to give ~1 µmol of material. This material was dissolved in 1 ml of water, and to this solution, 200 µl of concentrated ammonia was added. The solution was incubated overnight at room temperature, freeze-dried and compound 5 purified using RP-HPLC as described above with a yield of 0.6 µmol.

B. Synthesis of BODIPY-FL-PC-aadUTP from Intermediate Compounds

Compound 5 (0.23 µmol) was dissolved in 100 µl of 50 mM $NaHCO_3$ and then 73 µl of a 25 mM solution of BODIPY-FL-SE in dimethylformamide (DMF) (Molecular Probes Cat. No. D-2184) was added. The reaction mixture was incubated for two hours at room temperature and the product isolated using RP-HPLC as described above. Fractions containing the desired product were pooled and freeze-dried to give 36 nmoles of compound 6 (based on BODIPY-FL fluorophore absorption, Absorption max=505 nm, $\epsilon$=80,000).

Compound 6 was further characterized by photocleavage and HPLC analysis as well as absorption spectra extracted from the HPLC traces. For each of these experiments, approximately 2 nmoles of the material (i.e. compound 6) was used. The results of these experiments are depicted in FIGS. 6 and 8.

EXAMPLE 2

Synthesis of Photocleavable Cy5 Deoxyuridine Triphosphate (Cy5-PC-aadUTP)

In this example, one method for the production of the photocleavable marker-nucleotide conjugate, Cy5-PC-aadUTP (compound 7), is described.

Compound 5 (0.24 µmol), as prepared above, was dissolved in 40 µl of 50 mM $NaHCO_3$, followed by the addition of 0.72 µmol of a Cy5-NHS (Amersham-Pharmacia Biotech Cat. No. PA 25001) solution in 100 µl of DMF. The reaction mixture was incubated for 2 hours at room temperature and the product was isolated using RP-HPLC initially on R2/10 RP column (Perseptive Biosystems, 4.6×100 mm) followed by another purification on NovaPak C18, (Waters, 10×100 mm). In both case a gradient (0–90%) of acetonitrile in 50 mM triethylammonium acetate (pH 4.5) over 45 minutes with flow rate 1 ml/min. was used. Fractions containing the desired product were pooled and freeze-dried to give 60.5 nmoles of compound 7 (based on Cy5 fluorophore 550 nm absorption maximum, $\epsilon$=250,000).

Compound 7 was further characterized by photocleavage and HPLC analysis as well as absorption spectra extracted from the HPLC traces. For each of these experiments, approximately 2 nmoles of the material (i.e. compound 7) was used. The results of these experiments are depicted in FIGS. 6 and 8.

EXAMPLE 3

Enzymatic Incorporation of BODIPY-FL-PC-aadUTP into DNA and Photocleavage

In this example, one method for the incorporation of photocleavable marker-nucleotide into a nucleic acid (or polynucleic acid) to form a photocleavable marker-polynucleotide conjugate is described. Although the example below specifies the usage of BODIPY-FL-PC-aadUTP, it is important to note that the present invention also contemplates a method for the incorporation of photocleavable marker-nucleotide into a nucleic acid (or polynucleic acid) to form a photocleavable marker-polynucleotide conjugate wherein Cy5-PC-aadUTP is substituted in place of BODIPY-FL-PC-aadUTP (i.e. the method below will work equally well with either photocleavable marker nucleotide).

The enzymatic incorporation of a photocleavable marker-nucleotide into the oligonucleotide was performed using components of commercially available kit (Amersham-Pharmacia Biotech, Gene Images 3'-oligolabeling kit, Cat. No. RPN 5770) per the manufacturers instructions.

Briefly, an oligodeoxynucleotide (30-mer) having the sequence: 5'-GTA-TCT-ATA-TTC-ATC-ATA-GGA-AAC-ACC-ACA-3' (SEQ ID NO: 1) was used. This primer is useful for the amplification of a fragment of the human CFTR (Cystic Fibrosis Transmembrane Regulator) gene.

A volume of 10 μl of oligodeoxynucleotide (25 pmoles), water (5.8 μl), BODIPY-FL-PC-aadUTP (0.38 nmol, 1.25 μl), cacodylate buffer (2 μl) and terminal deoxynucleotidyl transferase (TdT) were mixed in a 500 μl microcentrifuge tube and incubated at 37° C. for 1 hour. An aliquot (1 μl) of the mixture was loaded on a denaturing 7M urea/15% polyacrylamide gel and imaged using a fluorescence scanning device (FluorImager, Molecular Dynamics). A control experiment utilizing Fluoreseein-11-dUTP was also performed and analyzed on the same gel. The results of these experiments are shown in FIG. 10. Both in the control experiment (Fluorescein-11-dUTP) and in the experiment utilizing BODIPY-FL-PC-aadUTP, a generation of several fluorescent bands were observed. These are most likely due to addition of multiple labels on the 3'-end by terminal transferase.

Figure 11:
FIG. 11 depicts one example of the incorporation of compound 6 into an oligonucleotide and fluorescent marker removal after incorporation followed by separation on 7M urea/15% polyacrylamide gel and fluorescent imaging. Lane 1—labeling with BODIPY-FL-PC-dUTP; lane 2—labeling with BODIPY-FL-PC-dUTP followed by UV light irradiation of the reaction mixture prior to gel analysis.

In a separate experiment an aliquot of BODIPY-FL-PC-aadUTP labeled DNA was subjected to near UV irradiation (300–365 nm, ~1 mW/cm$^2$)(BlakRay XX-15, UVP, Inc., San Gabriel, Calif.) for 5 minutes prior to gel analysis and imaging. The results of this experiment are depicted in FIG. 11. The fluorescent signal observed in BODIPY-FL-PC-aadUTP labeled oligonucleotide disappears completely after UV irradiation, which indicates that the fluorescent label has been removed (i.e. cleaved off) during UV irradiation.

c) removing said protective group from said photocleavable linker-nucleotide conjugate under conditions such that an activated photocleavable linker-nucleotide conjugate is created, wherein said activated photocleavable linker-nucleotide conjugate has an exposed reactive site on the linker portion of the conjugate; and d) contacting said activated marker molecule with said activated photocleavable linker-nucleotide conjugate under conditions such that a marker-photocleavable linker-nucleotide conjugate is produced.

2. The method of claim 1, wherein said protective group is selected from the group consisting of Fmoc and Bpoc.

3. The method of claim 1, wherein said amino-nucleotide analog is 5-(3-aminoallyl)-2'-deoxyuridine 5'-triphosphate.

4. The method of claim 1 further comprising: p1 e) contacting said marker-photocleavable linker-nucleotide conjugate of step (d) with a modifying enzyme, in the presence of nucleic acid, under conditions such that said marker-photocleavable linker-nucleotide conjugate is incorporated into said nucleic acid to produce a labeled nucleic acid.

5. The method of claim 4, further comprising f) detecting said incorporated marker of said marker-photocleavable linker-nucleotide conjugate in said labeled nucleic acid.

6. The method of claim 5, further comprising, prior to step f), the step of separating unincorporated marker-photocleavable linker-nucleotide coiijugate from said labeled nucleic acid.

7. The method of claim 4, further comprising the step of removing the incorporated photocleavable marker from said labeled nucleic acid by exposing said labeled nucleic acid to electromagnetic radiation so as to create a treated nucleic acid.

We claim:

1. A method of preparing a marker-photocleavable linker-nucleotide conjugate comprising:

a) providing i) a photocleavable linker comprising a protective group, ii) an amino-nucleotide analog, and iii) an activated marker molecule selected from the group consisting of BODIPY-FL-SF and Cy5-NHS;

b) operably linking said photocleavable linker to said amino-nucleotide analog to produce a photocleavable linker-nucleotide conjugate;

8. The method of claim 7, further comprising subjecting said treated nucleic acid to a further subsequent labeling reaction with a different marker-photocleavable linker-nucleotide conjugate after said removing step.

9. The method of claim 4, wherein said nucleic acid-modifying enzyme is a terminal deoxynucleotidyl transferase.

10. The marker-photocleavable linker-nucleotide conjugate produced according to claim 1.

11. A marker-photocleavable linker-nucleotide conjugate of the structure:

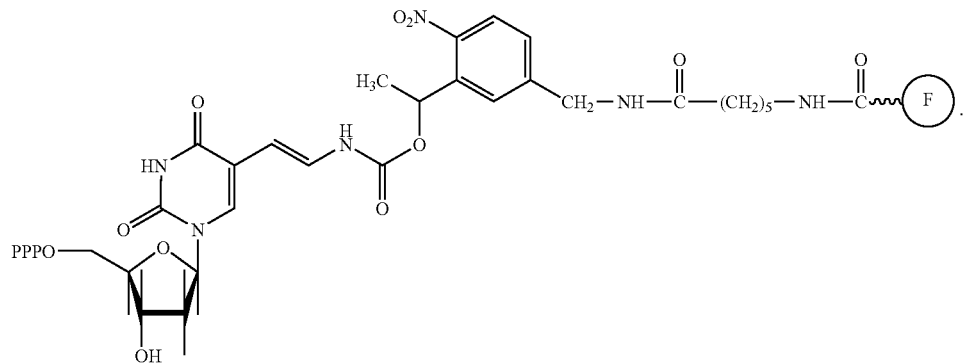
wherein F is a fluorophore marker and PPP is:
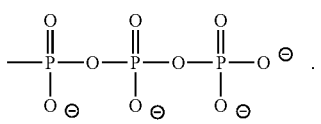
* * * * *